United States Patent [19]

Sakurai et al.

[11] 4,155,742

[45] May 22, 1979

[54] WATER-SOLUBLE BINDER

[75] Inventors: Akira Sakurai, Sakura; Yoshimi Tsuchiya, Yachiyo; Mikio Kanno, Tokyo, all of Japan

[73] Assignee: Kao Soap Co., Ltd., Tokyo, Japan

[21] Appl. No.: 870,414

[22] Filed: Jan. 18, 1978

[30] Foreign Application Priority Data

Feb. 14, 1977 [JP] Japan ................... 52-14722

[51] Int. Cl.$^2$ ..................... A01N 9/00; A01N 11/00
[52] U.S. Cl. .............................................. 71/67; 71/3; 71/33; 71/646 F; 252/89 R; 252/95; 252/106; 260/37 EP; 260/830 R; 424/76; 424/78; 528/87; 528/418; 252/259.5; 568/606; 568/622
[58] Field of Search ............ 260/830 R, 2 EP, 37 EP, 260/615 B; 424/78, 76; 71/67, DIG. 1, 3, 33, 646 F; 252/89 R, 95, 106; 528/418, 87; 239/54, 60

[56] References Cited

U.S. PATENT DOCUMENTS

| | | | |
|---|---|---|---|
| 3,182,099 | 5/1965 | Clark et al. ................... | 260/830 R |
| 3,236,622 | 2/1966 | Hartley et al. .................. | 424/78 |
| 3,275,518 | 9/1966 | Endicott et al. ................. | 424/78 |
| 3,308,082 | 3/1967 | Pauli et al. ..................... | 424/78 |

*Primary Examiner*—J. Ziegler

*Attorney, Agent, or Firm*—Blanchard, Flynn, Thiel, Boutell & Tanis

[57] ABSTRACT

A unit dosage form comprising one or more active ingredients and a water-soluble binder in which the water-soluble binder comprises, as a main component, a product obtained by condensing a polyoxyethylene alkyl, alkylphenyl or alkenyl ether having the following formula (I):

$$R\text{-}O\text{-}(CH_2CH_2O)_n H \qquad (I)$$

wherein R is alkyl or alkenyl having 8 to 22 carbon atoms or alkylphenyl group having 8 to 22 carbon atoms in the alkyl group, and n is an integer of from 50 to 500, with 1-epoxyethyl-3,4-epoxycyclohexane having the following formula (II):

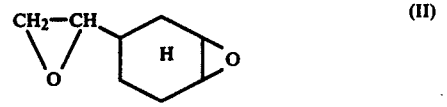

the molar ratio of the compound of the formula (II) to the compound of the formula (I) being in the range of from 0.05 to 2.5.

9 Claims, No Drawings

WATER-SOLUBLE BINDER

BACKGROUND OF THE INVENTION

1. Field of the Invention

The present invention relates to a water-soluble binder. More particularly, the invention relates to a water-soluble binder which can be mixed with various active ingredients and such mixtures can be molded into various shapes to provide unit dosage forms. When such unit dosage forms are placed in water, the binder dissolves in the water at a certain rate while constantly releasing the active ingredient.

In the following description and claims, the term "unit dosage form" means a physically discrete solid shape containing a predetermined quantity of one or more active ingredients effective for treating a material to obtain a beneficial result, but excluding the therapeutic treatment of human beings and animals. In addition to the active ingredients, the unit dosage form contains a water-soluble binder and various optional materials such as fillers, perfumes, coloring agents and the like.

2. Description of the Prior Art

As water-soluble binder bases for unit dosage forms, there have heretofore been used, for example, polyethylene glycol having a molecular weight of from 1,000 to 6,000, polypropylene glycol having a molecular weight of from 1,000 to 6,000, mixtures thereof, and water-soluble high-melting-point nonionic surface active agents which are solid at normal ambient temperature.

When these substances are used as binders, they become swollen when they are immersed in water for a long time, surface portions thereof are dissolved away in the slurry state and the active components are released into the water at a rapid rate. Accordingly, it is impossible to maintain a constant rate of release of the active components over a long time period and, therefore, the desired action of the active ingredient cannot last for a long time. In short, they have the disadvantage that the rate of release of the active components changes depending on the length of time that the unit dosage form has been in contact with water. Moreover, some of the previously used binders readily foam or bubble when they are placed in water and these bubbles persist for a long time. This bubbling action is not wanted in some applications.

The present invention overcomes the foregoing disadvantages of the conventional binders.

It is a principal object of the present invention to provide a binder which has a property such that when a unit dosage form containing the binder and one or more active ingredients is placed in water, the active components are not released at an excessively rapid rate and do not completely dissolve in a short time, but rather, they are released into the water at a substantially constant rate over a long period of time, whereby the activities of the active components can be maintained at predetermined levels for a long time. The binder has a much lower tendency to bubble and it can be used with a variety of active components.

More specifically, in accordance with the present invention, there is provided a water-soluble binder comprising, as a main component, a product obtained by condensing a polyoxyethylene alkyl, alkylphenyl or alkenyl ether having the following formula (I):

$$R-O-(CH_2CH_2O)_nH \quad (I)$$

wherein R is alkyl or alkenyl having 8 to 22 carbon atoms or alkylphenyl having 8 to 22 carbon atoms in the alkyl group, and n is an integer of from 50 to 500, with 1-epoxyethyl-3,4-epoxycyclohexane having the following formula (II):

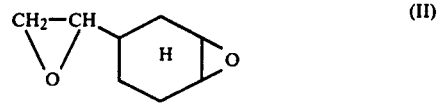

wherein the molar ratio of the compound of the formula (II) to the compound of the general formula (I) is in the range of from 0.05/1.0 to 2.5/1.0.

The condensation product of the formula (I) compound and the formula (II) compound (which condensation product is hereinafter sometimes referred to as "PAEH"), that is used as the main component of the binder of the present invention, can be obtained by a process comprising blowing ethylene oxide into a higher alcohol or alkylphenol of the formula ROH, wherein R has the same meaning as defined above, at about 100° C., in the presence of an alkali catalyst such as NaOH or KOH, whereby to add a predetermined amount of ethylene oxide to the higher alcohol or alkylphenol to form the formula (I) substance, adding a predetermined amount of 1-epoxyethyl-3,4-epoxycyclohexane of the above formula (II) dropwise to the resulting formula (I) adduct over a period of 1 to 3 hours in the presence of an alkali catalyst such as those mentioned above, and conducting the reaction for several hours. After completion of the reaction, the reaction product is neutralized with an appropriate acid, such as acetic acid, whereby to obtain PAEH used in the present invention.

The water-solubility of the binder of the present invention can be changed by varying the molar ratio of the formula (II) compound to the formula (I) compound in the PAEH used as the main component, and also by varying the carbon number of R in the formula (I) and the mole number "n" of added ethylene oxide. In order to attain the object of the present invention, it is critical that the molar ratio of 1-epoxyethyl-3,4-epoxycyclohexane of the formula (II) to the polyoxyethylene alkyl, alkenyl or alkylphenyl ether of the formula (I) should be in the range of from 0.05/1.0 to 2.5/1.0, preferably in the range of from 0.2/1.0 to 0.7/1.0. As this molar ratio becomes higher, the water solubility of the PAEH product is decreased, and if this molar ratio exceeds 2.5, the water solubility is too low and good results cannot be obtained. Similarly, the alkyl, the alkenyl and the alkyl moiety of the alkylphenyl group, used as R in the formula (I) compound, have 8 to 22 carbon atoms, preferably 14 to 22 carbon atoms, and the mole number n of added ethylene oxide is in the range of from 50 to 500, preferably in the range of from 150 to 250.

The PAEH condensation product is heated and melted, optional additives such as an extender are added to the melt according to need, and then the active ingredient or ingredients, selected according to the intended purpose of the unit dosage form, are added and mixed in the melt. Then, the resulting homogeneous melt is cooled to room temperature and is thereby solidified or the melt is molded into any desireable unit dosage form shape and is solidified. Alternatively, the melt is cast into a mold having an appropriate shape and is cooled and solidified. Thus, a unit dosage form containing the water-soluble binder of the present invention is formed.

The water-soluble binder of the present invention can be molded into any suitable unit dosage form shape containing therein various active components. When the unit dosage form is placed into water or aqueous liquids, the contained active components are gradually released at substantially constant rates over a long period of time. Accordingly, the active components are selected appropriately, depending on the intended purpose of use of same, so that the water-soluble binder of the present invention can be used in various fields. Some examples of applications of the water-soluble binder of the present invention are as follows:

(1) Solid Fungicide for Swimming Pools and the Like

If a fungicide is added directly to swimming pool water, the fungicidal effect initially attained at the time of application cannot be maintained for a long time. When a unit dosage form containing a mixture of the binder of the present invention and the fungicide, prepared as described above, is placed into the water, a substantially uniform fungicidal effect can be maintained continuously for a long time.

(2) Algicide Agent for Swimming Pools, Ponds, Industrial Cooling Water and the Like When a solid product containing the binder of the present invention and an algicide agent is used, generation of harmful algae and various growths can be prevented for a long time.

For the purposes (1) and (2), benzethonium chloride, benzalkonium chloride and the like can be used as the fungicide or algicide agent.

(3) Fragrant Detergent for Water Tanks of Flush Toilets

The binder of the present invention is melted and is mixed with a perfume, an appropriate water-soluble surface active agent for exerting a cleaning effect and a dye for imparting a pleasing clear color to the water, and the molten mixture is cooled and solidified. When the resulting product is placed in a suitable container and the container is hung in the water tank of a flush toilet of the tank type, every time the toilet is flushed, water containing the perfume, the surface active agent and the dye is flushed into the toilet bowl and fragrance-imparting, deodorizing and detergent effects can be attained. Any of the conventional perfumes that can be used in this field may be selected and used, but in general, the use of terpineol, p-dichlorobenzole, camphor and borneol is preferred.

(4) Fertilizer, Herbicide and Other Agricultural Chemicals for Agricultural Fields, such as Rice Paddy Fields It is generally preferred that a fertilizer, a herbicide or the like be applied to a field so that a certain concentration of the active ingredient or ingredients can be maintained for a long time. A product meeting this requirement can be prepared by solidifying a fertilizer, a herbicide or the like together with the binder of the present invention. When the thus-formed product is divided into granules having a size of several millimeters and these granules are scattered on a field, the fertilizer or other active ingredient is gradually dissolved out by ground water and/or rain water and the intended effect can be obtained for a long time.

(5) Dip Type Bleaching and/or Sterilizing Detergent

A surface active agent and a fungicide or bleaching agent are incorporated into the molten binder of the present invention, and the molten mixture is solidified in the form of a tablet or the like. The thus-formed tablet is placed in water and a cloth, such as a diaper or underwear, or other article to be subjected to a sterilizing or bleaching treatment, is dipped in the resulting detergent solution. Thus, the intended sterilizing or bleaching effect can be attained effectively. Since this detergent is solid (for example, in the form of a tablet), it can be handled very easily and the effect can be maintained for a long time.

Of course, applications of the water-soluble binder of the present invention are not limited to the above-mentioned specific examples.

The unit dosage form contains an amount of the binder effective for binding together the other ingredients to form a unitary solid shape which does not easily break apart during normal handling. Usually the amount of the binder is from about 5 to 80% by weight, based on the total weight of the unit dosage form.

The unit dosage form contains an amount of active ingredient or ingredients effective to achieve the desired treatment. The amount of active ingredient is variable depending on the particular ingredient used and the concentration thereof needed to obtain the desired result.

The unit dosage form of the present invention may further comprise up to about 40% by weight of water-soluble inorganic salt, for example, sodium sulfate or sodium carbonate, as a filler or extender.

The present invention will now be further described in detail by reference to the following illustrative examples.

EXAMPLE 1

In the presence of 10 g of calcium hydroxide as an alkali catalyst, 1780 g of polyoxyethylene alkyl ether of the formula (I) having 16 carbon atoms in the alkyl group, in which the mole number of added ethylene oxide "n" was 200, was reacted with 13 g of 1-epoxyethyl-3,4-epoxycyclohexane of the formula (II) for 3 hours, and then the pH of the reaction mixture was adjusted to 7.0 by addition of acetic acid, whereby to obtain PAEH. In the thus-prepared PAEH, the molar ratio of the compound of the formula (II) to the compound of the formula (I) was ¼. In separate tests, the thus-prepared PAEH and, for comparison, a conventional polyethylene glycol or nonionic surface active agent, was used as a binder, and it was heated and melted at 80° C. The surface active agent, perfume, dye and other components shown in Table 1 were added to the melt and homogeneously mixed therein. Then, a sample of 10 g of the molten mixture was cooled and solidified to form a tablet of a fragrant detergent for use in the water tanks of flush toilets. The thus-prepared detergent was immersed in 100 cc of water maintained at 20° C., and 10 ml samples of the water were removed every 10 minutes and the percent transmission of radiation of a wave length of 630 m$\mu$ was measured as a factor indicating the amount of the fragrant detergent that was dissolved in the water. A smaller percent transmission indicates a larger amount of the detergent was dissolved in the water sample. The results obtained are shown in Table 2.

Changes of percent transmission were measured with passage of time. At zero minutes, the transmission was assigned the arbitrary value of 100. At the various times set forth in table 2, the transmissions relative to the starting transmission are listed.

Table 1

| Components | Comparison | | | Present Invention | | |
|---|---|---|---|---|---|---|
| | Sample A | Sample B | Sample C | Sample D | Sample E | Sample F |
| polyethylene glycol (average molecular weight = 6000) | 60 | | 30 | | | |
| PAEH | | | | 50 | 50 | 30 |
| nonionic surface active agent*1 | 23 | 60 | 30 | | | |
| sodium sulfate | | 23 | 23 | 33 | 23 | 23 |
| sodium citrate | 5 | 5 | 5 | 5 | 5 | 5 |
| perfume | 10 | 10 | 10 | 10 | 10 | 10 |
| dye (blue) | 2 | 2 | 2 | 2 | 2 | 2 |
| water | | | | | 10 | 30 |

*1: polyoxyethylene (50) nonylphenyl ether

Table 2

| Sample | Change of Percent Transmission with Passage of Time | | | | | | | |
|---|---|---|---|---|---|---|---|---|
| | Dipping Time | | | | | | | |
| Comparison | 30 minutes | 1 hour | 2 hours | 3 hours | 5 hours | 7 hours | 12 hours | 24 hours |
| A | 83 | 74 | 60 | 57 | 49 | 41 | 31 | 16 |
| B | 78 | 53 | 48 | 43 | 39 | 31 | 20 | 9 |
| C | 80 | 72 | 53 | 50 | 45 | 39 | 27 | 14 |
| Present Invention | | | | | | | | |
| D | 98 | 89 | 84 | 80 | 76 | 69 | 60 | 56 |
| E | 95 | 91 | 87 | 83 | 80 | 77 | 73 | 71 |
| F | 96 | 87 | 86 | 80 | 75 | 72 | 68 | 63 |

As is apparent from the results shown in Table 2, in fragrant detergents for flush toilets prepared by using the conventional excipient (samples A to C), the dissolved-out amounts are extremely large, especially during a short period in the initial stage of dipping, whereas in fragrant detergents according to the present invention (samples D to F), the dissolved-out amounts are small and even after passage of a long time, the dissolved-out amounts are almost constant and suitable concentrations are maintained.

EXAMPLE 2

Various kinds of PAEH, differing in the carbon atom number of the alkyl group, were prepared in the same manner as described in Example 1, and the water solubility characteristics of the resulting binders were tested with respect to the following composition in the same manner as described in Example 1.

| Composition (% by weight): | |
|---|---|
| PAEH | 30 |
| Sodium sulfate | 23 |
| Sodium citrate | 5 |
| Perfume | 10 |
| Dye | 2 |
| Water | 30 |

The results obtained are shown in Table 3.

Table 3

| Carbon Number of Alkyl Group (R) of PAEH *1 | Change of Percent Transmission with Passage of Time | | | | | | |
|---|---|---|---|---|---|---|---|
| | Dipping Time | | | | | | |
| | 30 minutes | 1 hour | 3 hours | 5 hours | 7 hours | 12 hours | 24 hours |
| 8 | 85 | 70 | 59 | 53 | 50 | 43 | 35 |
| 10 | 90 | 75 | 69 | 65 | 59 | 51 | 46 |
| 12 | 95 | 80 | 73 | 70 | 67 | 60 | 54 |
| 14 | 95 | 84 | 77 | 74 | 70 | 63 | 61 |
| 16 | 96 | 87 | 80 | 75 | 72 | 68 | 63 |
| 18 | 98 | 90 | 88 | 83 | 80 | 79 | 70 |

*1
n = 200
polyoxyethylene alkyl ether/1-epoxyethyl-3,4-epoxycyclohexane molar ratio = 2/1

As is apparent from the results shown in Table 3, as the carbon atom number increases, the water solubility is reduced and the dissolution is more uniform.

EXAMPLE 3

Various kinds of PAEH differing in the mole number "n" of added ethylene oxide were prepared in the same manner as described in Example 1, and the water solubility characteristics of the resulting binders were tested with respect to the following composition in the same manner as described in Example 1.

| Composition (% by weight): | |
|---|---|
| PAEH | 50 |
| Sodium sulfate | 23 |
| Sodium citrate | 5 |

| Composition (% by weight): | |
|---|---|
| Perfume | 10 |
| Dye (blue) | 2 |
| Water | 10 |

The results obtained are shown in Table 4.

Table 4

| Mole Number (n) of Added Ethylene Oxide in PAEH *1 | Change of Percent Transmission with Passage of Time |  |  |  |  |  |  |
|---|---|---|---|---|---|---|---|
| | Dipping Time | | | | | | |
| | 30 minutes | 1 hour | 3 hours | 5 hours | 7 hours | 12 hours | 24 hours |
| 30 | 97 | 94 | 93 | 90 | 88 | 85 | 83 |
| 50 | 96 | 90 | 88 | 86 | 85 | 82 | 80 |
| 150 | 95 | 89 | 84 | 82 | 80 | 76 | 73 |
| 250 | 95 | 87 | 85 | 80 | 78 | 76 | 70 |
| 500 | 93 | 83 | 82 | 76 | 71 | 69 | 60 |
| 600 | 90 | 76 | 74 | 68 | 62 | 58 | 42 |

*1
alkyl (R) of polyoxyethylene alkyl ether in PAEH = $C_{16}H_{33}$
polyoxyethylene alkyl ether/1-epoxyethyl-3,4-epoxycyclohexane molar ratio = 2/1

As is apparent from the results shown in Table 4, when the mole number of added ethylene oxide in PAEH is in the range of from 50 to 500, a water solubility suitable for ordinary applications is obtained. If the mole number is smaller than 50, the solubility is reduced, and if the mole number exceeds 500, the solubility becomes too high.

EXAMPLE 4

Various kinds of PAEH differing in the molar ratio of the polyoxyethylene alkyl ether of the formula (I) to 1-epoxyethyl-3,4-epoxycyclohexane of the formula (II) were prepared in the same manner as described in Example 1, and the water solubility characteristics of the resulting binders were examined with respect to the following composition in the same manner as described in Example 1.

| Composition (% by weight): | |
|---|---|
| PAEH | 50 |
| Sodium sulfate | 33 |
| Sodium citrate | 5 |
| Perfume | 10 |
| Dye (blue) | 2 |

The results obtained are shown in Table 5.

Table 5

| Reaction Molar Ratio M [M = (I)/(II)] | Change of Percent Transmission with Passage of Time |  |  |  |  |  |  |
|---|---|---|---|---|---|---|---|
| | Dipping Time | | | | | | |
| | 30 minutes | 1 hour | 3 hours | 5 hours | 7 hours | 12 hours | 24 hours |
| 2/0.1 | 90 | 79 | 73 | 65 | 60 | 52 | 40 |
| 2/0.5 | 92 | 88 | 77 | 70 | 64 | 55 | 49 |
| 2/1.0 | 98 | 89 | 80 | 76 | 69 | 60 | 51 |
| 2/3.0 | 98 | 90 | 87 | 84 | 79 | 73 | 70 |
| 2/5.0 | 98 | 90 | 88 | 86 | 84 | 82 | 80 |

Note:
In the polyoxyethylene alkyl ether of PAEH, the alkyl group R was $C_{16}H_{33}$ and the mole number n of added ethylene oxide was 200.

From the results shown in Table 5, it is seen that as the reaction molar ratio M of the polyoxyethylene alkyl ether to 1-epoxyethyl-3,4-epoxycyclohexane is lowered, the water solubility is reduced and that a water solubility desirable for the intended use can be obtained by adjusting the reaction molar ratio M appropriately.

EXAMPLE 5

| Composition (% by weight): | |
|---|---|
| PAEH *1 | 35 |
| Sodium sulfate | 25 |
| Fungicide (sold under registered trademark "Irgasan CF3" | 5 |
| Water | 35 |

*1
In the polyoxyethylene alkyl ether of PAEH, the alkyl group R was $C_{16}H_{33}$ and the mole number n of added ethylene oxide was 200, and the polyoxyethylene alkyl ether/1-epoxy-ethyl-3,4-epoxycyclohexane molar ratio in PAEH was 2/0.5.

PAEH was melted at 80° C., and the other three components were added to the melt and the mixture was agitated to form a homogeneous molten mixture. Then, the molten mixture was placed in a plastic container. When the thus-prepared product was dipped in water, a substantially uniform fungicidal effect was maintained for a long time.

EXAMPLE 6

| Composition (% by weight): | |
|---|---|
| PAEH *1 | 30 |
| Cationic surface active agent (stearyldimethylbenzyl ammonium chloride) | 40 |
| Sodium citrate | 5 |
| Perfume | 5 |
| Dye (blue) | 2 |
| Water | 18 |

*1
In the polyoxyethylene alkyl ether of PAEH, the alkyl group R was $C_{18}H_{37}$ and the mole number n of added ethylene oxide was 250, and the polyoxyethylene alkyl ether/1-epoxy-ethyl-3,4-epoxycyclohexane molar ratio in PAEH was 2.0/1.0.

In the same manner as described in Example 5, PAEH was first melted at 80° C. and the other components except the perfume were added. While the mixture was being agitated uniformly, it was cooled and at 60° C. the perfume was added to the mixture. Then, the mixture was filled in a vessel and solidified to form a fragrant detergent tablet for a flush toilet. The detergent was charged into a plastic container which was then set in a flush toilet. Substantially uniform deodorizing and fungicidal effects were maintained for a long time with a good fragrance.

The water-soluble binder of this invention can be applied to various compositions. Embodiments of them will be described below.

1. a detergent composition with a pleasing smell suitable for cleaning and maintaining a pleasant odor in flush toilets.

| PAEH | 5.0 to 80 wt %, preferably 30 to 60 wt % |
|---|---|
| active surfactant | 2.0 to 30 wt %, preferably 5 to 20 wt % |
| perfume | 2.0 to 30 wt %, preferably 10 to 20 wt % |
| filler | 5.0 to 40 wt %, preferably 20 to 30 wt % |

2. a solid fungicide or algicide composition suitable for treating swimming pool water and industrial cooling water

| PAEH | 5.0 to 80 wt %, preferably 30 to 60 wt % |
|---|---|
| fungicide or algicide | 1 to 50 wt %, preferably 20 to 30 wt % |
| filler | 5 to 40 wt %, preferably 20 to 30 wt % |

3. a solid fertilizer or herbicide composition

| PAEH | 5.0 to 80 wt %, preferably 30 to 60 wt % |
|---|---|
| fertilizer or herbicide | 10 to 60 wt %, preferably 30 to 50 wt % |
| filler | 5 to 40 wt %, preferably 20 to 30 wt % |

4. a dip type detergent composition

| PAEH | 5.0 to 80 wt %, preferably 30 to 60 wt % |
|---|---|
| active surfactant | 10 to 60 wt %, preferably 20 to 40 wt % |
| filler | 5 to 40 wt %, preferably 20 to 30 wt % |

As surface active agents, there can be used polyoxyethylene alkylethers, polyoxyethylene nonylphenylethers, polyoxyethylene acylesters, soaps of aliphatic acids, sulfates of higher alcohols, benzalkonium chloride and benzetonium chloride.

As to fillers, there are used sodium sulfate, potassium sulfate, ammonium sulfate, sodium phosphate, potassium phosphate, ammonium carbonate, sodium carbonate, potassium carbonate and sodium citrate.

As to fungicides and algicides, there are used benzalkonium chloride, benzetonium chloride, alkyldiaminoethylglycine hydrochloric acid salt, Irgasan DP 300 and Irgasan CF₃ (the last two are products manufactured by Ciba-Geigy Ltd.).

As fertilizers, there are used ammonium sulfate, superphosphate of lime and potassium sulfate.

As to herbicides, there are used 2,4-dichlorophenoxyacetate, isopropyl N-phenylcarbamate and sodium dinitro-o-cresolate.

The embodiments of the invention in which an exclusive property or privilege is claimed are defined as follows:

1. A solid unit dosage form comprising a mixture of one or more active ingredients and a water-soluble binder, said water-soluble binder being a reaction product obtained by condensing
(A) a material having the formula

wherein R is alkyl having 8 to 22 carbon atoms, alkenyl having 8 to 22 carbon atoms or alkylphenyl in which the alkyl has 8 to 22 carbon atoms, and n is an integer of from 50 to 500 with (B) 1-epoxyethyl-3,4-epoxycyclohexane, wherein the molar ratio of B/A is in the range of from 0.05/1.0 to 2.5/1.0.

2. A solid unit dosage form as set forth in claim 1 in which R is alkyl having 14 to 22 carbon atoms, alkenyl having 14 to 22 carbon atoms or alkylphenyl in which the alkyl has 14 to 22 carbon atoms, and n is an integer of from 150 to 250.

3. A solid unit dosage form as set forth in claim 1 wherein the molar ratio of B/A is in the range of from 0.2/1.0 to 0.7/1.0.

4. A solid unit dosage form as set forth in claim 1 containing from 5 to 80 percent by weight of said water-soluble binder, an effective amount of said active ingredient and up to 40 percent by weight of inert filler material.

5. A solid unit dosage form as set forth in claim 4 prepared by melting said water-soluble binder, blending the other ingredients in the molten binder, and then cooling the molten binder to solidify it and forming the blend into a unit dosage form shape.

6. A solid unit dosage form as set forth in claim 1 consisting essentially 5 to 80 percent by weight of said binder, from 2 to 30 percent by weight of water-soluble solid organic surfactant, from 2 to 30 percent by weight of perfume and 5 to 40 percent by weight of water-soluble solid inert filler.

7. A solid unit dosage form as set forth in claim 1 consisting essentially of from 5 to 80 percent by weight of said binder, from 1 to 50 percent by weight of fungicide or algicide and from 5 to 40 percent by weight of water-soluble solid inert filler.

8. A solid unit dosage form as set forth in claim 1 consisting essentially of from 5 to 80 percent by weight of said binder, from 10 to 60 percent by weight of fertilizer or herbicide and from 5 to 40 percent by weight of water-soluble solid inert filler.

9. A solid unit dosage form as set forth in claim 1 consisting essentially of from 5 to 80 percent by weight of said binder, from 10 to 60 percent by weight of water-soluble organic surfactant and from 5 to 40 percent by weight of water-soluble solid inert filler.

* * * * *